United States Patent [19]

Dean et al.

[11] Patent Number: 5,144,043
[45] Date of Patent: Sep. 1, 1992

[54] CLEAVABLE BIFUNCTIONAL COUPLING AGENTS

[75] Inventors: Richard T. Dean, Downingtown, Pa.; Raymond H. Boutin, Wilmington, Del.; Robert W. Weber, Downingtown, Pa.

[73] Assignee: Centocor, Malvern, Pa.

[21] Appl. No.: 235,999

[22] Filed: Aug. 24, 1988

Related U.S. Application Data

[63] Continuation-in-part of Ser. No. 207,261, Jun. 15, 1988.

[51] Int. Cl.$^5$ .................................. C07D 207/448
[52] U.S. Cl. .................................................. 548/548
[58] Field of Search ........................................ 548/548

[56] References Cited

FOREIGN PATENT DOCUMENTS 0173629 8/1985 European Pat. Off. .

OTHER PUBLICATIONS

Khaw, et al., *Science*, 209, 295-97 (1980).
Krejcarek, et al., *Biochem. Biophys. Res. Comm.*, 77, 581-585 (1977).
Childs, et al., *J. Nucl. Med.*, 26, 293 (1985).
Fritzberg, et al., *J. Nucl. Med.*, 27, 957-958 (1986).
Quadri, et al., *J. Nucl. Med.*, 27, 959 (1986).
Yokoyama, et al., *J. Nucl. Med.*, 28, 572 (1987).
Paik, et al., *J. Nucl. Med.*, 29, 889 (1988).
Paik, et al., *J. Nucl. Med.*, 28, 602 (1988).
Deshpande, et al., *J. Nucl. Med.*, 29, 922-923 (1988).
Optimum Conditions for Labeling of DTPA-Coupled Antibodies with Technetium-99m by R. L. Childs and D. J. Hnatowich pp. 293-299 (1985).

*Primary Examiner*—David B. Springer
*Attorney, Agent, or Firm*—Woodcock Washburn Kurtz Mackiewicz & Norris

[57] ABSTRACT

A bifunctional coupling agent for joining a sulfhydryl containing protein or peptide and a metallic radionuclide comprising a sulfhydryl selective electrophile, a chelator containing at least one protected thiol and a organic linking radical containing at least one cleavable site which serves to join said electrophile and said chelator is disclosed. A radiodiagnostic or radiotherapeutic precursor comprising an antibody or antibody fragment and the specified bifunctional coupling agent bound to a sulfhydryl group on the antibody or antibody fragment and a radiodiagnostic or radiotherapeutic agent comprising such precursor having a metallic radionuclide bound thereto are also disclosed.

6 Claims, No Drawings

CLEAVABLE BIFUNCTIONAL COUPLING AGENTS

CROSS-REFERENCE TO RELATED APPLICATIONS

This application is a continuation-in-part of copending and commonly-assigned U.S. Ser. No. 207,261, filed Jun. 15, 1988, now pending and entitled "Bifunctional Coupling Agents and Radionuclide Labeled Compositions Prepared Therefrom".

BACKGROUND OF THE INVENTION

This invention relates to the fields of radiolabeled proteins, radioimmunotherapy and immunodiagnostics and, more particularly, to methods for labeling antibodies and fragments thereof with radiometals.

The attachment of radiometals to proteins, especially antibodies and antibody fragments, results in the formation of new radiodiagnostic and radiotherapeutic agents. The performance of the radiometal-protein conjugates depends on a number of factors, such as the stability of the radiometal-protein bond in the conjugates and the ability of the conjugates to localize to the target tissue. Clearly, since it is desired that radioactive agent not accumulate in any but the target tissues, the performance of such agents also depends in great part on the extent and rate at which the agents are eventually cleared from non-target tissue.

The use of monoclonal antibodies and antibody fragments in protein-radiometal conjugates should ideally provide an efficient means of localizing such conjugates to target tissue. Monoclonal antibodies are highly specific and can be used, for example, for imaging specific target sites or as vehicles to deliver other substances to such target sites. In recent years, numerous antibodies have been developed with affinity for targets such as atherosclerotic tissue, fibrinogen, myosin, and tumors, to name just a few, and work in this area continues.

Proteins and antibodies have been shown to form stable bonds to radiometals by the use of bifunctional coupling agents. The bifunctional agent is selected such that it is capable of binding radiometals by chelation and also form a stable linkage to the protein. Thus, the protein or antibody is bound to the radiometal through the bifunctional coupling agent. For example, diethylenetriaminepentaacetic acid (DTPA) has been conjugated onto an antimyosin antibody, and the protein-bound DTPA used to chelate indium-111 (Khaw, et al., *Science*, 209, 295-97 (1980). See also Krejcarek, et al., *Biochem. Biophys. Res. Comm.*, 77, 581-85 (1977) and Childs, R. L. and Hnatowich, D. J., *J. Nucl. Med.*, 26, 293 (1985)). This approach has also been used where particular diaminodithiol and diamidedithiol chelating agents have been coupled to antibodies (Fritzberg, et al., *J. Nucl. Med.*, 27, 957-58 (1986) and Eary, J., et al., *J. Nucl Med.*, 28, 650-51 (1987)). Chelated radiometals and bifunctional coupling agents have been linked to proteins by lysyl side chain amino groups (EPO Publication No. 188, 256). Chelators have also been site-selectively attached to oxidized antibody carbohydrate moieties (EPO Publication No. 173,629, U.S. Pat. No. 4,671,958). Chelators can also be attached by reaction with free sulfhydryl groups (U.S. Pat. No. 4,659,839, U.S. Pat. No. 4,671,958 and EPO Publication No. 173, 629).

Although means have been found for preparing stable protein-radiometal conjugates which effectively localize to target tissue, the dosage of such conjugates to non-target tissue is a factor which limits the dosage at which the conjugates may be used. The clearance of radiometallated antibodies by the use of a cleavable bifunctional coupling agent has been addressed. DTPA derivatives containing cleavable functionalities have been used to form conjugates between indium-111 and antibodies. This composition has an increased clearance rate in mice (Quadri, S. M., et al., *J. Nucl. Med.*, 27, 959 (1986), Yokoyama, K., et al., *J. Nucl. Med.*, 28, 572 (1987) and Paik, C. H., et al., *J. Nucl. Med.*, 29, 889 (1988)). The bifunctional agent was linked to the antibodies by lysyl side chain amino groups. The antibody-linked chelator was labeled with indium-111, and purification was required prior to use.

Radiometals other than indium are particularly well-suited for use in immunodiagnostic and immunotherapeutic procedures. Technetium-99m, for example, is one such radiometal because of its nuclear properties (single photon energy of 140 KeV, a half-life of about 6 hours) and ready availability. There is therefore a need for protein-radiometal conjugates using radiometals such as technetium which are more readily cleared from non-target tissues than conjugates previously disclosed. There is also a need for such conjugates which can be prepared by simple methods e.g., by methods not requiring purification steps and which do not decrease the affinity of the radiolabeled protein.

SUMMARY OF THE INVENTION

It has now been found that decreased accumulation of a radiolabeled protein or peptide, labelled with radiometals such as Tc-99m, in non-target tissues, especially the excretory organs such as the liver and kidneys, can be accomplished by the use of a radiolabeled material in which the radiometal is coupled to a sulfhydryl-site on said protein or peptide through a bifunctional coupling agent containing a cleavable site. This invention relates to novel bifunctional coupling agents which comprise a sulfhydryl-selective electrophile, a chelator containing at least one protected thiol and an organic linking radical containing at least one cleavable site which serves to join said sulfhydryl-selective electrophile and said chelator. The invention further relates to a radiodiagnostic or radiotherapeutic precursor comprising an antibody or antibody fragment having the above-described bifunctional coupling agent bound to a sulfhydryl group thereon. Still further, the invention relates to a radiodiagnostic or radiotherapeutic agent comprising the above-mentioned precursor and a metallic radionuclide bound to a thiol group on said precursor.

The novel bifunctional coupling agents of this invention are advantageous for a number of reasons. One advantage of these coupling agents stems from the fact that free sulfhydryl sites on biologically functional proteins such as antibodies are usually distal to the antigen binding sites. Since the claimed coupling agents are selectively bound to sulfhydryl sites on the antibody or fragment, the accompanying radionuclide chelator is removed from the antigen binding region of that antibody, thus reducing the likelihood of interference of the chelator with antibody-antigen binding. Another advantage of the claimed coupling agents is that their use results in decreased accumulation of the radiolabeled protein or peptide in tissues other than that which comprises the specific binding target of the protein or peptide.

DETAILED DESCRIPTION OF THE INVENTION

The bifunctional coupling agents of the invention can be represented by the general formula E - L - C, wherein E is a sulfhydryl selective electrophile, L is an organic linking radical containing at least one cleavable functional group, and C is a chelator containing at least one protected thiol.

The sulfhydryl-selective electrophile, E, is that portion of the bifunctional coupling agent which forms a bond with the protein to be labelled Suitable electrophiles include any functionality capable of forming a stable bond with a protein sulfhydryl in the presence of other reactive groups normally found on proteins. Examples of sulfhydryl-selective electrophiles include those in the group consisting of haloalkyl, sulfonate ester, maleimide and aziridine. Preferably, the sulfhydryl selective electrophile is selected from the group consisting of $ClCH_2CONH-$, $BrCH_2CONH-$, $ICH_2CONH-$ and N-substituted maleimide.

The chelator, C, is that portion of the bifunctional coupling agent which forms a bond with the radionuclide, and this moiety contains at least one protected thiol group. Normally, a thiol-containing chelating moiety in a bifunctional coupling agent would be incompatible with a sulfhydryl-selective electrophilic moiety in the same agent. The thiol-containing chelating moiety is therefore suitably protected from reaction with the electrophilic moiety during attachment of the bifunctional coupling agent to the protein substrate. As used herein, the expression "protected thiol" refers to a thiol-containing moiety wherein the thiol group(s) is(are) reversibly derivatized such that the thiol(s) is(are) rendered unreactive. After attachment to the protein substrate the chelating moiety can be deprotected to unmask the chelating functionality for radionuclide binding.

Groups suitable for protecting the thiol from reaction are organic or inorganic groups which can be readily removed under mild conditions (described in more detail hereinafter) to regenerate the free thiol in the presence of the protein without substantially altering the activity of the protein. In preferred embodiments of the invention, the thiol protecting group is selected from the group consisting of thiol esters, disulfides and Michael-addition products. More preferably the protecting group is a thiol ester.

Preferably the chelator is one of the formula:

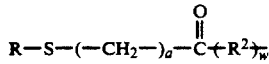

wherein a is an integer from 1 to 3 inclusive, and most preferably 1; R is $R^1CO-$ or $R^1S-$, wherein $R^1$ is methyl, optionally substituted lower alkyl, and optionally substituted aryl, and most preferably R is $R^1CO-$ wherein $R^1$ is phenyl or phenyl substituted with a functional group; each $R^2$ is, independently, selected from the units

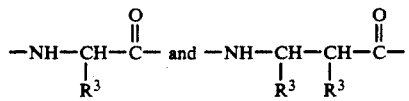

and w is an integer from 3 to 6 inclusive, and preferably $R^2$ is $-NHCH(R^3)CO-$units; and w is 3; each $R^3$ is independently selected from hydrogen, optionally substituted lower alkyl, optionally substituted aryl, and most preferably $R^3$ is hydrogen or hydroxymethyl. The term "alkyl" as used herein includes branched and straight chain alkyl groups, and "lower alkyl" refers to such groups having up to six carbon atoms. The term "optionally substituted" as used herein refers to optional substitution with functional groups, such as but not limited to alkoxy groups, alkyl groups, aryl groups, hydroxy groups, and carboxy groups, which will not interfere with the desired coupling and labelling reactions. Generally speaking, such functional groups are unreactive to reaction with mercaptans, sulfides, amines and alkylating agents.

The organic linking radical, L, has at least two valencies for joining the electrophilic moiety E and the chelating moiety C. The organic linking radical also contains a cleavable site, thus enhancing clearance of the radiometal from non-target tissue. As used herein, the expression "cleavable site" refers to a chemical bond in the linking radical, the breaking of which bond serves to dissociate the radiometal in chelated form from the labelled protein, which bond is known to have an appreciable rate of dissociation in neutral aqueous media or known to have an appreciable rate of dissociation by metabolism in an organ. Such dissociation should preferably occur at a rate of at least about 50% within the half-life of the radiometal.

The organic linking radical can optionally contain more than one cleavable site. The cleavable site can be part of the organic linking radical or can form one of the bonds joining the organic linking radical to the chelating moiety and/or the electrophilic moiety. Most preferably the cleavable site is an alkyl ester or an aryl ester. Preferred organic linking radicals are selected from the group consisting of optionally substituted alkyl, optionally substituted alkyl containing heteroatom substituents for carbon (e.g., in which a carbon in the aliphatic chain is substituted with a heteroatom such as N, O or S), and optionally substituted aryl groups. Most preferably the organic linking radical is selected from those of the formula:

$$-X-(CH_2)_b$$
$$-(OCH_2CH_2)_c-(Y)_q-(CH_2)_d-(OCH_2CH_2)_e-$$

wherein b is an integer from 0 to 6 inclusive, and preferably 2; d and e are independently integers from 0 to 5 inclusive, and preferably 2; c is an integer from 0 to 5 inclusive, and preferably 1; q is 0 or 1; X is selected from the group consisting of $-NH-$, $-O-$ or $-S-$, and preferably $-O-$; Y is selected from the group consisting of $-CH_2COO-$, $-OOCCH_2-$, $-CH_2CONH-$, $-OCH_2COO-$, $-NHCOCH_2-$, and $-OOCCH_2O-$, and is preferably $-OCH_2COO-$; provided that, when X is other than $-O-$, then q is 1 and Y is other than $-CH_2CONH-$ or $-NHCOCH_2-$.

Preferred bifunctional coupling agents of the invention are represented by the following formulae:

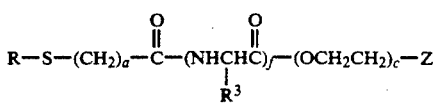

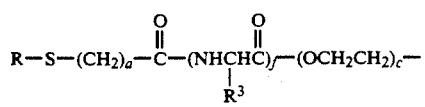

-continued

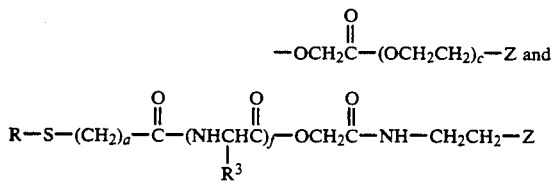

wherein a is an integer from 1 to 3 inclusive; c is an integer from 1 to 7 inclusive; f is an integer from 3 to 6 inclusive; R is $R^1CO-$ or $R^1S-$, wherein $R^1$ is selected from optionally substituted lower alkyl, and optionally substituted aryl; $R^3$ is selected from hydrogen, optionally substituted lower alkyl, and optionally substituted aryl; and Z is selected from $ClCH_2CONH-$, $BrCH_2CONH-$, $ICH_2CONH-$ or N-substituted maleimide.

The bifunctional coupling agents of this invention are useful for binding an antibody or antibody fragment with a radiometal having an affinity for thiols. Useful radionuclides include isotopes of Tc, Re, Pb and Cu. The bifunctional coupling agents are useful for the preparation of compositions of the formula Ab-S-E-L-C-M, wherein Ab is an antibody or fragment derived therefrom, S is a sulfhydryl, M is a radiometal having affinity for thiols, and E, L, and C are defined above.

As stated above, the bifunctional coupling agents of this invention can be used to selectively attach a radionuclide to a sulfhydryl-containing group on a protein. Sulfhydryls on proteins are due to the presence of cysteine residues. Other amino acids and functionalities in the protein can be left unmodified. Proteins containing a free sulfhydryl group can be conjugated directly to the bifunctional coupling agent. Many proteins do not possess sulfhydryl groups but do contain disulfide bonds as cystine amino acids. These disulfide bonds can be reduced to free cysteines by mild reducing agents. Among suitable reducing agents are dithiothreitol, dithioerythritol, cysteine, mercaptoethanol or a variety of other reducing agents. Optimal use of the invention includes the purification of the reduced protein. This purification can be achieved by standard methods, usually by gel filtration chromatography. A representative reduction would be addition of sufficient dithiothreitol to give a 2-20 mM concentration, addition being to a 1-10 mg/mL solution of protein in a buffer at pH 7 to 8. After approximately one hour the protein is passed down a gel filtration column in the buffer desired for reaction with the bifunctional coupling reagent.

In a preferred embodiment, the bifunctional coupling agents of this invention are employed to join a radionuclide and an antibody molecule or fragment. Intact antibodies do not normally possess free cysteine, but do contain cystine disulfides. An intact antibody can therefore be joined to the bifunctional coupling agent after reduction as described above. Intact antibodies can also be treated with a proteolytic enzyme, such as pepsin, to give an antigen binding fragment $F(ab')_2$ and another fragment $F_c$. The $F(ab')_2$ can be split into two Fab' fragments by mild reduction as described above. This Fab' contains both an antigen binding site as well as free cysteine thiol groups. The antigen binding properties of the Fab' are unaffected by reaction with the bifunctional reagent, as the section of the protein comprising the antigen binding site does not react with the bifunctional reagent.

The bifunctional coupling agent is added to the protein solution in an excess relative to the number of free sulfhydryls to prepare a radiodiagnostic or radiotherapeutic precursor. Typically to a 1-2 mg/mL solution of protein in a buffer at pH 7 to 8, preferably pH 7.0, is added the bifunctional coupling agent in a co-solvent such as dimethylsulfoxide or dimethylformamide, if required. The agent is present in a 5-15 molar ratio to the number of sulfhydryl groups. If a co-solvent is necessary to solubilize the agent, the concentration of the co-solvent is kept between 1 and 15% v/v, usually around 5%. A reaction time of 1 to 2 hours is generally sufficient to react all of the sulfhydryls present, longer reaction times than this are not optimal. Excess bifunctional coupling agent is then removed. Usually this is accomplished using gel filtration chromatography.

Using mild conditions, the thiol protecting groups are then removed from the bifunctional coupling agent which is attached to the protein. For the disulfide protected thiols this can be accomplished by the same conditions used to reduce protein disulfides as described above. Protecting groups which can be removed by retro-Michael reaction need only have the pH of the media increased. The thiol esters can be removed by exposure to reagents generally known to be nucleophilic in neutral aqueous solutions. This can include hydroxide, imidazole, hydrazine and substituted hydrazines and hydroxylamine and substituted hydroxylamines. A typical procedure for the removal of a thiol ester would be to treat a volume of the protein solution with a volume of 0.5-1.0 M hydroxylamine at or near pH 7.5 for a period of 5 minutes. The protein can then be purified by gel filtration chromatography.

Deprotection of the bifunctional coupling agent-protein conjugate provides a thiol-containing chelating functionality for the binding of metals, especially radionuclides. The affinity of the deprotected chelating portion for metals is generally high enough that this binding can be accomplished in aqueous solution near neutral pH and at or near ambient temperatures. A pH range of 5-8 and temperatures of 4° to 37° C. can be used.

Some radionuclides require a change in oxidation state prior to complexing with the bifunctional coupling agent. The change in oxidation state can be accomplished either in a separate vessel or in the presence of the bifunctional coupling agent-protein conjugate. Depending on the nature of the radionuclide, and the relative speed of complex formation, a transfer-ligand may be required. This transfer-ligand consists of a molecule or mixture capable of weakly complexing the radionuclide in a reduced state. This transfer ligand is intended only to transiently stabilize an otherwise relatively unstable intermediate. The technetium complex of the bifunctional coupling agent can be prepared in this fashion using D-glucaric acid as a transfer ligand. The eluate from a technetium-99m generator is mixed with an equal volume of 20 to 30 mg/mL monopotassium D-glucaric acid in 0.2 N bicarbonate. A reducing agent is then added, usually a 5 uL/mL addition of 5 mg/mL stannous chloride in 0.2 N aqueous acetic acid. After waiting an appropriate length of time for the pertechnetate to reduce and the transfer complex to form, the mixture is mixed with the deprotected bifunctional coupling agent-protein conjugate. The protein conjugate is usually in a buffered solution at pH 7 to 8. The mixture is allowed to sit at or near ambient temperature until more than 90% and usually more than 95%, of the technetium becomes attached to the protein. This can be ascertained by a variety of quantitative and qualitative methods including gel filtration HPLC and thin layer chromatography techniques.

The following are examples of specifically preferred bifunctional coupling agents of the invention.

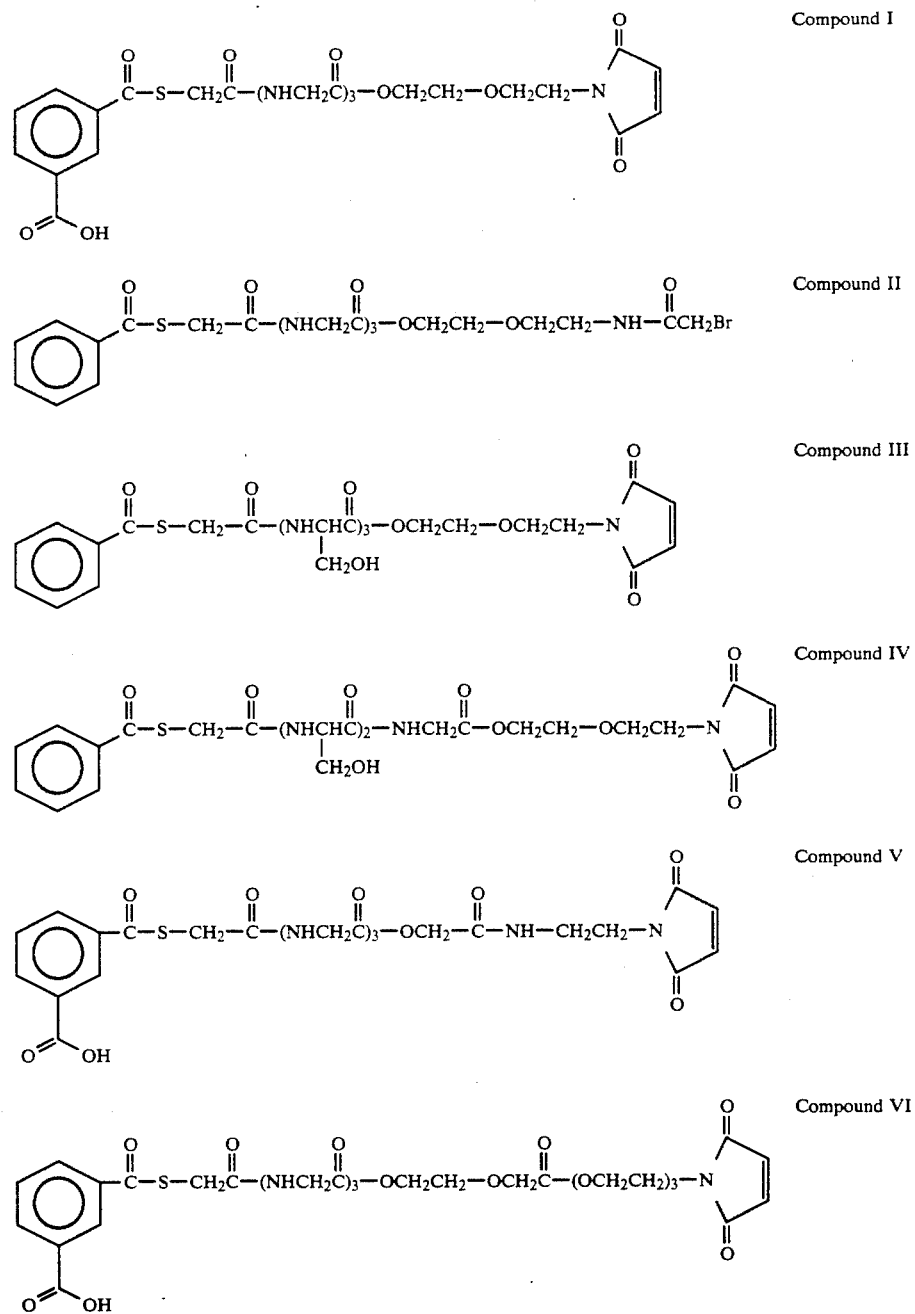

Compound I can be readily prepared according to the following scheme:

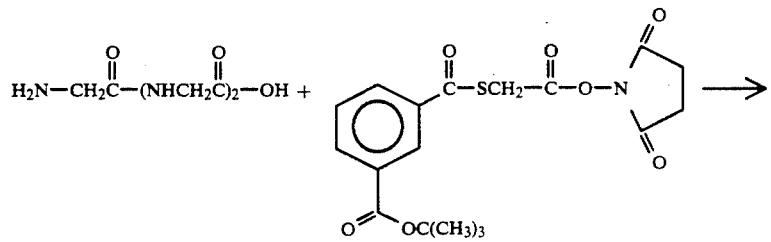

-continued
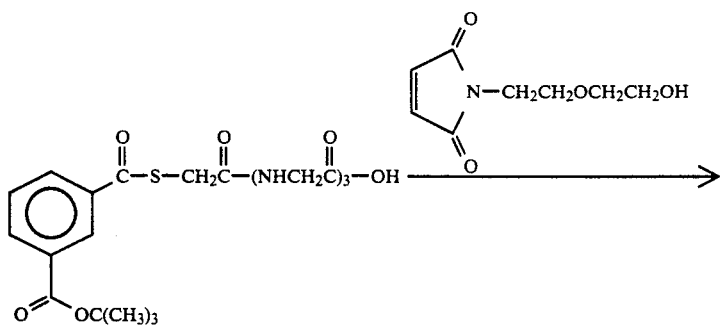
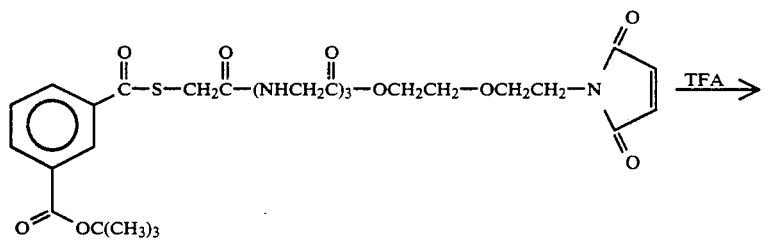
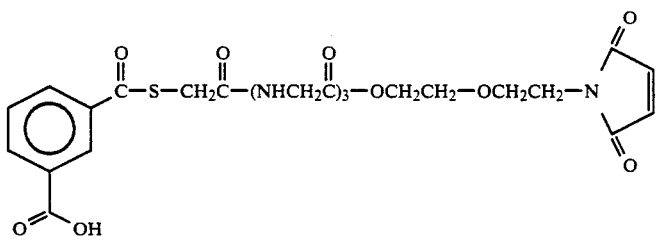
Compound II can be readily prepared according to the following scheme:
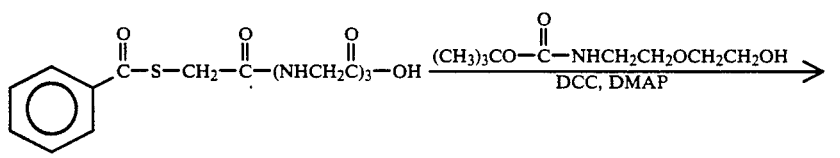
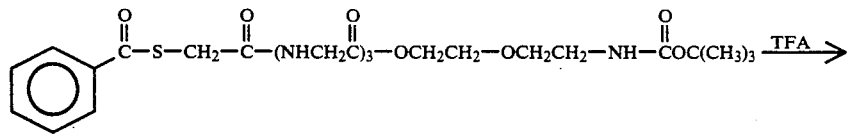
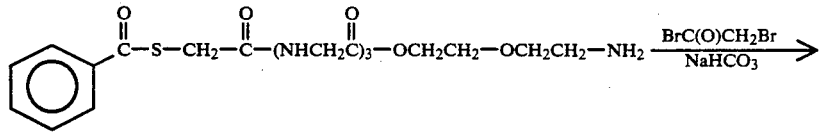
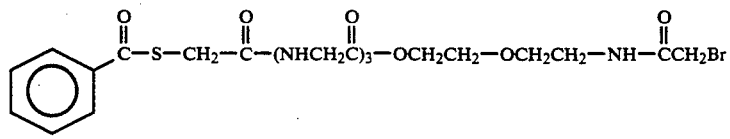
Compound III can be readily prepared according to the following scheme:

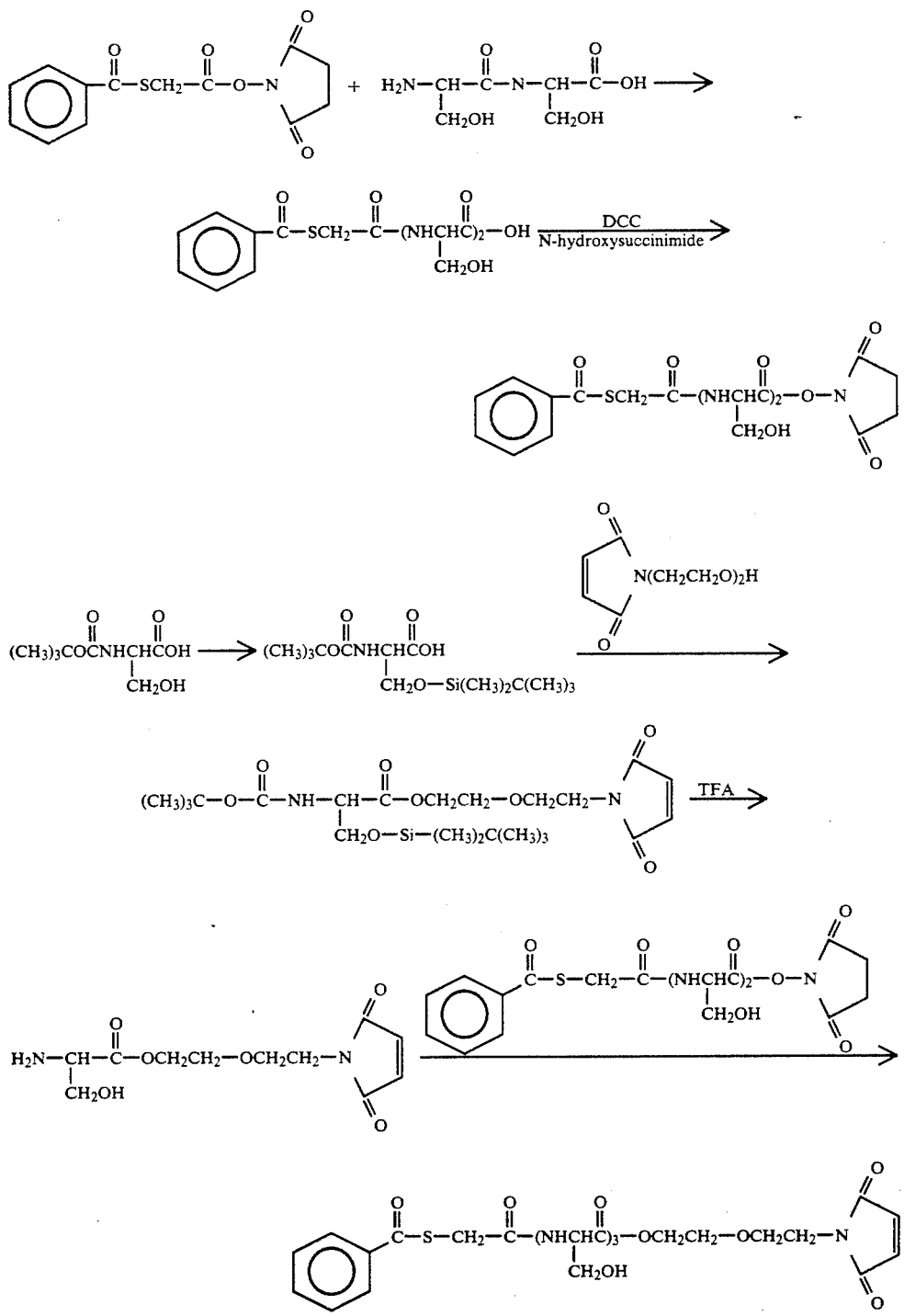
Compound IV can be readily prepared according to the following scheme:
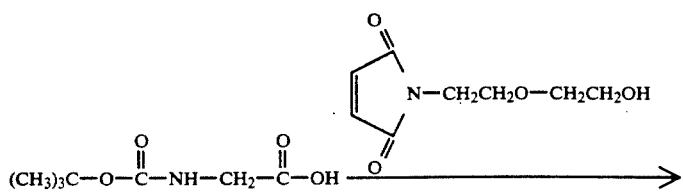

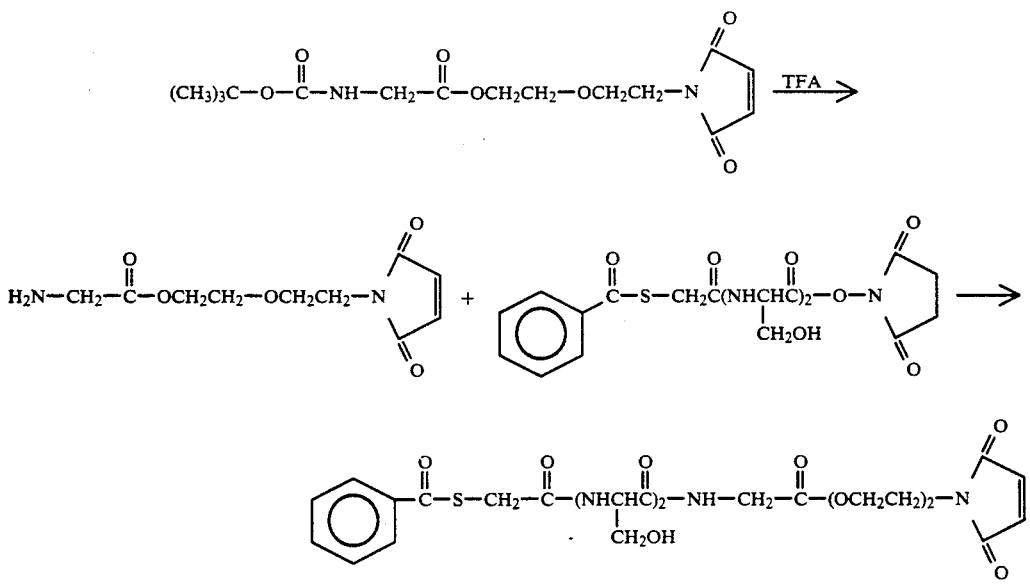
Compound V can be readily prepared according to the following scheme:
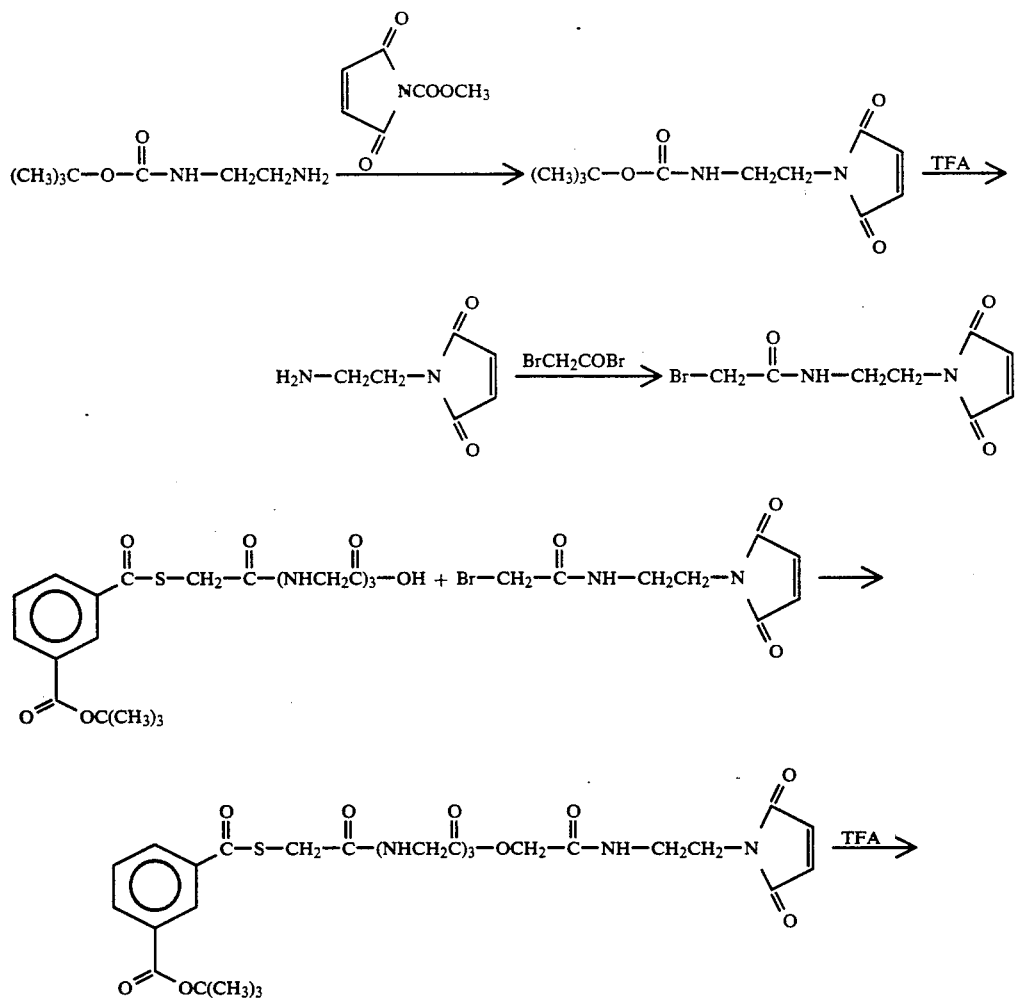

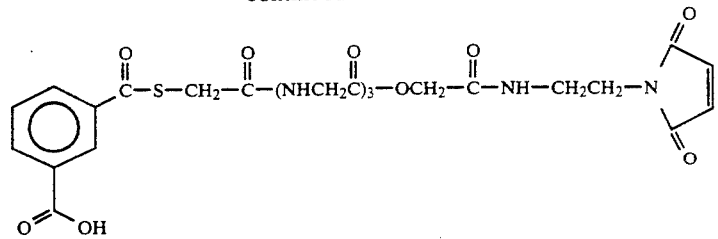
Compound VI can be readily prepared according to the following scheme:
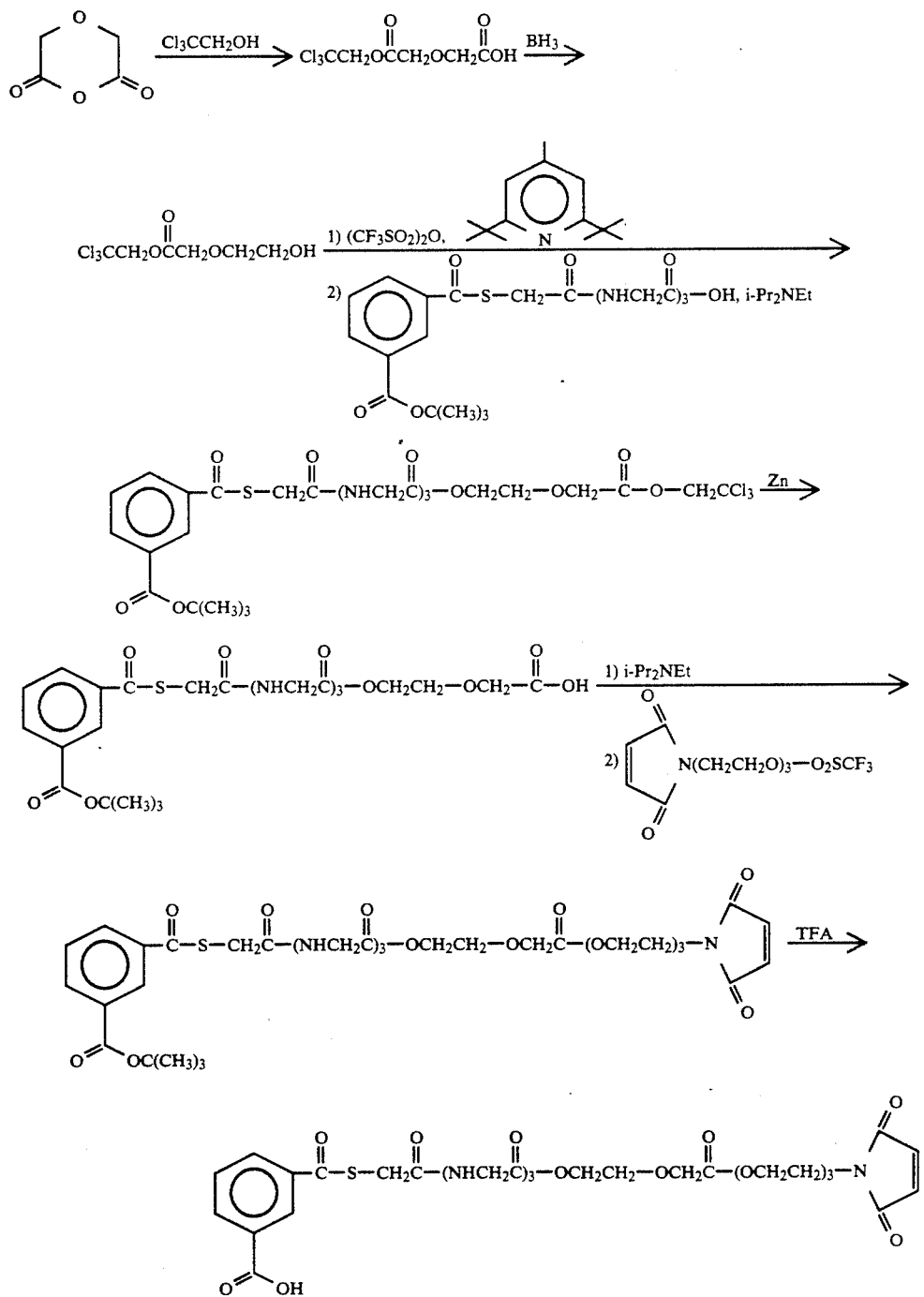

EXAMPLES

The invention is further described in the following examples. All temperatures are degrees Celsius. NMR spectra are given for $^1$H at 300 MHz using TMS as an internal standard.

EXAMPLE I

Preparation of 2-(2-maleimidoethoxy)ethyl (2-(3-carboxybenzoylthio)acetyl)glycylglycylglycinate (Compound I)

a) Preparation of (2-(3-tert-butyloxycarbonylbenzoylthio)acetyl)glycylglycylglycine.

A solution of triglycine (0.53 g, 2.8 mmoles) and NaHCO$_3$ (0.26 g, 3.0 mmoles) in water (10 mL) was cooled in an ice bath and treated with a solution of succinimidyl 3-tert-butyloxycarbonylbenzoate (1.1 g, 2.8 mmoles) (Fritzberg, A. R. Eur. Pat Appl. 86100360.6) in THF (10 mL). After stirring at 0° C. for 30 minutes, the mixture was stirred at room temperature for 1 hour. THF was removed under reduced pressure, and the aqueous mixture was acidified to pH 3 with 1 N HCl. The resulting precipitate was collected and recrystallized from aqueous acetone (0.55 g, 42%). NMR (DMSO-d$_6$) δ1.57 (s, 9H), 3.75 (m, 6H), 3.94 (s, 2H), 7.73 (t, 1H), 8.20 (m, 4H), 8.38 (s, 1H), 8.55 (t, 1H).

b) Preparation of 2-(2-maleimidoethoxy)ethanol.

A solution of 2-(2-aminoethoxy)ethanol (1.35 g, 13 mmoles) in saturated NaHCO$_3$ (65 mL) was cooled in an ice bath and treated with N-methoxycarbonyl maleimide (2.00 g, 13 mmoles). After 20 minutes, the ice bath was removed and the solution was stirred at room temperature for 30 minutes. The solution was extracted with CHCl$_3$ (3×50 ml) and the combined extracts were dried (Na$_2$SO$_4$). Removal of the solvent under reduced pressure gave the maleimido alcohol as an oil (1.70 g, 71%). NMR (CDCl$_3$)δ2.32 (t, 1H, —OH), 3.54 (m, 2H), 2.64 (m, 6H), 6.72 (s, 2H).

c) Preparation of 2-(2-maleimidoethoxy)ethyl (2-(3-tert-butyloxycarbonylbenzoylthio)acetyl)glycylglycylglycinate.

The above maleimido alcohol (80 mg, 0.43 mmoles) in CH$_2$Cl$_2$ (2 mL), cooled by an ice bath, was treated with 2, 6 di-t-butyl-4-methylpyridine (90 mg, 0.43 mmoles) followed by trifluoromethanesulfonic anhydride (120 mg, 0.43 mmoles) in CH$_2$Cl$_2$ (1 mL). After stirring 1 hour the precipitate was removed by filtration, and the filtrate was added to a solution of (2-(3-tertbutyloxycarbonylbenzoylthio)acetyl)glycylglycylglycine (200 mg, 0.43 mmoles) and diisopropylethylamine (75 μL, 0.43 mmoles) in CH$_2$Cl$_2$ (2 mL). After stirring for 2 hours the mixture was concentrated and chromatographed (SiO$_2$, CHCl$_3$-CH$_3$OH gradient) to give the ester (70 mg, 26%). NMR (CDCl$_3$) δ1.61 (s, 9H), 3.63 (m, 6H), 3.85 (s, 2H), 4.02 (m, 6H), 4.22 (t, 2H), 6.72 (s, 2H), 7.21 (t, 1H), 7.40 (t, 1H), 7.44 (t, 1H), 7.52 (t, 1H), 8.09 (d, 1H), 8.20 (d, 1H), 8.54 (s, 1H).

d) Preparation of 2-(2-maleimidoethoxy)ethyl (2-(3-carboxybenzoylthio)acetyl)glycylglycylglycinate.

The tripeptide ester prepared above (60 mg, 0.09 mmoles) was stirred with trifluoroacetic acid (2 mL) for 2 hours. TFA was removed at the vacuum pump to yield an oil which precipitated from CH$_3$OH to give the product (50 mg, 91%). NMR (DMSO-d$_6$) δ 3.58 (m, 6H), 3.79 (m, 6H), 3.92 (s, 2H), 4.08 (m, 2H), 7.03 (s, 2H), 7.72 (t, 1H), 8.21 (m, 3H), 8.43 (s, 1H), 8.52 (m, 1H).

EXAMPLE 2

Coupling of 2-(2-maleimidoethoxy)ethyl (2-(3-carboxybenzoylthio)acetyl)glycylglycylglycinate (Compound I) to Antifibrin.

a) Coupling of Compound I to Antifibrin Fab'.

Antifibrin Fab'(1 mL, 1.5 mg/mL) pH 7.0 in 0.10 M phosphate containing 1 mM EDTA was analyzed for sulfhydryl content. An aliquot (50μL) was removed and diluted to 1.0 mL with 0.01 M phosphate pH 8.0. To this was added 50 μL of 5 mg/mL 5,5'-dithiobis(2-nitrobenzoio acid) (DTNB, Ellman's reagent) in 0.10 M phosphate pH 8.0. The solution was mixed and A$_{412}$ measured after 15 minutes. Equivalents of sulfhydryl were determined from a molar absorption coefficient of 15,800 at 412 nm and a protein MW of 50,000. A value of 3.6 sulfhydryl/mole was determined. The remaining Antifibrin solution was treated with 10μL of 6.9 mg/110μL Compound I in DMF. The solution was mixed and allowed to stand at room temperature for 1.5 h. The reaction mixture was purified by Sephadex G-25 (medium) chromatography (1×10 cm), eluting with 0.10 M phosphate, pH 7.0, containing 1 mM EDTA. Fractions (1 mL) were collected and analyzed for protein concentration by A$_{280}$. As a chromophore had been added to the protein, the A280 readings gave only qualitative information. Aliquots (50μL) of the protein containing fractions were diluted to 1.0 mL with 0.01 M phosphate pH 8.0, and treated with DTNB as above. No absorption was found at 412 nm. Fraction 5 had A$_{280}$=1.69.

b) Removal of the S-benzoyl.

A solution of Compound I - Antifibrin conjugate (0.60 mL) was treated with 0.60 mL of 1.0 M NH$_2$OH.HCl in 0.5 M HEPES, pH 7.5 (adjusted with 50% NaOH). The solution was mixed and left at room temperature for 5 minutes. The mixture was purified by Sephadex G-25 (medium) chromatography (1 X 10 cm), eluting with 0.10 M phosphate pH 7.5 containing 1 mM EDTA. Fractions (1 mL) were collected and analyzed for protein concentration. Protein containing fractions were assayed for sulfhydryl content as above. Fraction 5 was found to contain 0.9 mg/mL with 2.3 sulfhydryls/mole.

EXAMPLE 3

Technetium Labeling of Antifibrin Modified with Compound I.

A vial was charged with 1 mL of a solution containing 0.2 M NaHCO$_3$, 12 mg/mL potassium D-glucarate, and 100 μg/mL SnCl$_2$ at pH 6.8. Following lyophilization, the residue was treated with sodium [Tc-99] pertechnetate solution (1 mL) from a Mo-99/Tc-99m generator. The solution was mixed and allowed to stand at room temperature for 15 minutes. To an aliquot of the deprotected Antifibrin-Compound I conjugate (500 μL) was added 500/μL of the [Tc-99m] technetium-glucarate solution. The solution was mixed and left at room temperature. After 15 minutes, chromatography on Whatman 3 MM paper eluted with acetonitrile/water 64/40 showed a single peak at the origin. HPLC showed 28% of the radioactivity at R$_t$ 8.9 [F(ab')$_2$] and 72% at R$_t$ 9.8 (Fab').

EXAMPLE 4

Biodistribution of Radiolabeled Antifibrin-Compound I Conjugate.

Biodistribution of the radiolabeled Antifibrin-Compound I conjugate was determined in mice. An aliquot of the labeled protein solution was diluted to 0.05 mg/mL at 0.25 mCi/mL with saline and filtered through a 0.2µm membrane filter. Mice were injected with 0.10 mL of the radioactive solution. At various time points, the mice (n=3) were sacrificed and the organs counted. The data are presented in Table 1.

TABLE 1

Mouse Biodistribution of Tc-99m Labeled Antifibrin-Compound I Conjugate

| Time (hrs.) | % dose/gram | | | | |
|---|---|---|---|---|---|
| | 0.5 | 1.0 | 2.5 | 5.0 | 24.0 |
| Organ | | | | | |
| Blood | 14.78 | 10.95 | 4.35 | 1.81 | 0.35 |
| Heart | 2.80 | 2.72 | 1.17 | 0.44 | 0.13 |
| Lungs | 4.68 | 4.51 | 1.67 | 0.94 | 0.26 |
| Liver | 3.78 | 3.36 | 1.93 | 1.20 | 0.76 |
| Spleen | 1.85 | 1.66 | 0.84 | 0.46 | 0.23 |
| Kidneys | 27.31 | 20.99 | 12.19 | 6.81 | 2.72 |
| Stomach | 1.41 | 0.92 | 0.50 | 0.89 | 0.38 |
| S.I. | 2.46 | 3.16 | 3.28 | 1.79 | 0.30 |
| L.I. | 0.64 | 0.53 | 4.53 | 4.34 | 1.09 |
| Muscle | 0.53 | 0.45 | 0.39 | 0.28 | 0.05 |

EXAMPLE 5

Preparation of 2-(2-(2-bromoacetamido)ethoxy)ethyl (2-benzoylthioacetyl)glycylglycylglycinate (Compound II).

a) 2-(2-tert-butyloxycarbonylaminoethoxy)ethanol.

To a solution of 15.78 g of 2-(2-aminoethoxy)ethanol (0.15 mole) in 500 mL of $CHCl_3$ was added dropwise a solution of 36.03 g of di-tert-butyl dicarbonate (0.17 mole, 110 mol%) in 50 mL of $CHCl_3$. The mixture was stirred for 24 hours at room temperature. The $CHCl_3$ was removed by rotary evaporator to give a clear, colorless oil. This oil was purified by Kugelrohr distillation (bp 80°, 1.0 mmHg) of the volatile impurities, leaving the less volatile product. Obtained 30.27 g, 0.15 moles, 98%.

b) preparation of 2-(2-tert-butyloxycarbonylaminoethoxy)ethyl (2-benzoylthioacetyl)glycylglycylglycinate.

To a suspension of 1.5 g (2-benzoylthioacetyl)glycylglycylglycine (Fritzberg, A. R., et al. *J. Nucl. Med.*, 27, 111–116 (1986)) (4.09 mmoles) in 60 mL of THF/DMF 1:1 was added 1.67 g of 2-(2-tert-butyloxycarbonylaminoethoxy)ethanol (8.17 mmoles, 200 mol%) followed by 0.84 g of dicyclohexylcarbodiimide (4.08 mmoles, 100 mol%) and 0.05 g of 4-dimethylaminopyridine (0.41 mmoles, 10 mol%). The heterogeneous mixture was stirred for 48 h at room temperature. The solid was filtered off, and the filtrate concentrated to give a yellow oil (rotary evaporator, aspirator followed by a vacuum pump, 35°). The oil was triturated with 15 mL of DMF, filtered, and 10 mL of water added to the filtrate. The cloudy solution was purified by flash chromatography on 80 mL of reverse phase (ODS) silica gel. The column was eluted with a methanol/water gradient. Removal of solvent gave a white powder which was dried under vacuum overnight to give 1.0 g (1.80 mmoles, 44%). TLC Rf 0.75 (MeOH/$H_2O$ 4:1 on ODS reverse phase plates). NMR (DMSO-$d_6$) δ 1.37 (s, 10H) 3.06 (t, 2H), 3.39 (t, 2H), 2.77 (m, 4H), 3.88 (m, 4H), 4.15 (t, 2H), 5.78 (t, 1H), 7.57 (t, 2H), 7.71 (t, 1H), 7.93 (d, 2H), 8.21 (m, 2H), 8.47 (t, 1H).

c) Preparation of 2-(2-(2-bromoacetamido)ethoxy)ethyl (2-benzoylthioacetyl)glycylglycylglycinate (Compound II).

The protected ester described above (0.33 g, 0.60 mmoles) was dissolved in 5 mL of trifluoroacetic acid and stirred for 1 h at room temperature. The trifluoroacetic acid was removed by rotary evaporator to give a pale yellow oil. This oil was dissolved in 25 mL of $CHCl_3$ and solvent removed to give an oil. The oil was dried under vacuum overnight to give a faintly yellow waxy solid. NMR indicated the complete loss of tert-butyl groups.

The crude amine prepared above (0.60 mmoles) was dissolved in 10 mL of $H_2O$ and cooled to 0°. To the solution was added 0.30 g of $NaHCO_3$ (3.57 mmoles, 600 mol%) followed by 0.10 mL of 2-bromoacetyl bromide (1.20 mmoles, 200 mol%). The reaction mixture was stirred for 30 min at 0. The resultant precipitate was filtered off and dried under vacuum to give 20 mg of a very slightly tan powder (0.35 mmoles, 6%). TLC $R_f$ 0.50 (2-propanol/$CHCl_3$ 1:4). NMR (DMSO-$d_6$, 300 MHz) δ3.24 (t, integral obscured by water peak), 3.43 (t, integral obscured by water peak), 3.59 (m, 2H), 3.77 (m, 4H), 3.86 (two s+m, 6H), 4.16 (m, 2H), 7.58 (t, 2H), 7.71 (t, 1H), 7.93 (d, 2H), 8.29 (m, 3H), 8.50 (t, 1H).

EXAMPLE 6

Coupling of Compound II to Antifibrin and Removal of the S-Benzoyl Group

Compound II was coupled to Antifibrin Fab' as detailed in Example 2. Treatment of the conjugate with $H_2NOH$ as above gave product with 1.9 sulfhydryl/mole.

EXAMPLE 7

Technetium Labeling of Antifibrin Modified with Compound II

A 26 mg/mL solution of D-glucaric acid in 0.10 M phosphate buffer was prepared and the pH adjusted to 7.50. To 1.0 mL of the glucaric acid solution was added 1.0 mL of [Tc-99m]pertechnetate (Mo-99/Tc-99m generator eluate, 40 mCi/mL) followed by 10 µL of a solution of 5.0 mg/mL stannous chloride in 0.2 N HOAc. The technetium-glucarate solution was mixed, then let stand for 5 min at room temperature. An aliquot of this solution was mixed with an equal volume of the deprotected Antifibrin-Compound II conjugate. After standing at room temperature for 15 minutes, gel filtration HPLC showed 100% protein bound radiolabel.

EXAMPLE 8

Biodistribution of Radiolabeled Antifibrin-Compound II Conjugate

Biodistribution data were obtained as described in Example 4, mouse biodistribution results are presented in Table 2.

TABLE 2

Mouse Biodistribution of Tc-99m Labeled Antifibrin-Compound II Conjugate

| Time (hrs.) | % dose gram | | | |
|---|---|---|---|---|
| | 0.5 | 1.0 | 4.0 | 24.0 |
| Organ | | | | |
| Blood | 15.22 | 8.72 | 2.23 | 0.55 |

TABLE 2-continued

Mouse Biodistribution of Tc-99m Labeled Antifibrin-Compound II Conjugate

| Time (hrs.) | % dose gram | | | |
|---|---|---|---|---|
| | 0.5 | 1.0 | 4.0 | 24.0 |
| Heart | 3.88 | 2.19 | 0.55 | 0.17 |
| Lungs | 3.67 | 2.70 | 0.87 | 0.33 |
| Liver | 4.99 | 4.69 | 3.04 | 1.70 |
| Spleen | 2.73 | 1.45 | 0.96 | 0.51 |
| Kidneys | 64.31 | 61.35 | 35.26 | 13.00 |
| Stomach | 1.15 | 1.48 | 0.86 | 0.22 |
| S.I. | 3.29 | 4.49 | 1.73 | 0.21 |
| L.I. | 1.02 | 1.19 | 5.87 | 0.42 |
| Muscle | 0.65 | 0.50 | 0.24 | 0.06 |

EXAMPLE 9

Preparation of 2-(2-maleimidoethoxy)ethyl N-(2-benzoylthioacetyl)serylserylserinate (Compound III).

a) Preparation of N-(2-benzoylthioacetyl)serylserine.

To a suspension of 0.50 g of L-seryl-L-serine (Bachem, 2.60 mmoles) in 5 mL of water and 5 mL of THF was added 1.10 g of NaHCO$_3$ (13.0 mmoles, 500 mol%) and 0.76 g of succinimidyl 2-benzoylthioacetate (2.60 mmoles, 100 mol%) (R. F. Schneider, et al., *J. Nucl. Med.*, 25, 223-29 (1984)). The mixture was stirred at room temperature for 2 h. The THF was removed by rotary evaporator (bath temperature <30°). Water (40 mL) was added and the pH adjusted to approximately 3 with 1 N HCl. The gelatinous mixture was placed in the refrigerator overnight, then filtered. The solid was dried under vacuum over P$_2$O$_5$ for 48 h. This gave the product as an impure white powder (0.18 g, 0.49 mmoles, 19%). NMR (DMSO-d$_6$) δ2.59 (N-hydroxysuccinimide), 3.57 (m, 4H), 3.89 (s, 2H), 4.18 (overlapping m, 1H), 4.39 (m, 2H), 7.55 (m, 6H, should be 4H), 7.92 (m, 4H, should be 2H), 8.38 (s, 1H), 8.72 (d, 0.5H, impurity).

b) Preparation of succinimidyl (2-benzoylthioacetyl)-serylserinate.

Crude (2-benzoylthioacetyl)serylserinate, prepared above (0.18 g, 0.49 mmoles), was suspended in 5 mL of DMF and 3 mL of THF. To this suspension was added 0.06 g of N-hydroxysuccinimide, (0.49 mmoles, 100 mol%) and 0.10 g of dicyclohexylcarbodiimide (0.49 mmoles, 100 mol%). The heterogeneous mixture was stirred at room temperature overnight. The mixture was filtered, and the filtrate concentrated by rotary evaporator (bath temperature <30°, water aspirator followed by vacuum pump) to give a tan solid. This was dried under vacuum for 48 h.

c) Preparation of N-t-BOC-3-0-tert-butyldimethylsilyl-L-serine.

N-tBOC-L-Serine (5.0 g, 24.4 mmoles) was dissolved in 75 mL of DMF. To this solution was added 7.47 mL of triethylamine (53.6 mmole, 220 mol%) followed by 8.08 g of tert-butylchlorodimethylsilane (53.6 mmoles, 220 mol%) and 0.83 g of imidazole (12.2 mmoles, 50 mol%). The reaction mixture was stirred overnight at room temperature. A solution of NaHCO$_3$ (0.2 N, 250 mL) was added, and the heterogeneous mixture stirred vigorously at room temperature for 1 h. The mixture was extracted with EtOAc (1×150 mL) and the organic layer discarded. The pH of the aqueous layer was adjusted to approximately 3.5 with 4 N HCl and extracted with EtOAc (3×150 mL). The combined extracts were dried over Na$_2$SO$_4$, filtered and solvent removed to give a clear liquid. TLC R$_f$0.28 (CHCl$_3$/2-propanol 19:1). NMR showed pure product and DMF. The DMF could not be removed by flash chromatography or by drying under vacuum over P$_2$O$_5$ (120 h) (4.70 g, 14.71 mmoles, 60%). NMR (DMSO-d$_6$) δ0.06 (s, 6H), 0.89 (s, 9H), 1.42 (s, 9H), 3.84 (d, 2H), 4.09 (dd, 1H), 6.70 (d, 1H).

d) Preparation of 2-(2-maleimidoethoxy) ethyl N-tBOC-3-0-(tert-butyldimethylsilyl)serinate.

The N-tBOC-serine derivative described above (1.10 g, 3.45 mmoles) was dissolved in 20 mL of THF. To the solution was added 0.64 g of 2-(2-maleimidoethoxy)-ethanol (3.45 mmoles, 100 mol%), 0.71 g of dicyclohexylcarbodiimide (3.45 mmoles, 100 mol%) and 0.04 g of 4-dimethylaminopyridine (0.35 mmoles, 10 mol%). The pink solution was immediately placed in the freezer and let stand overnight. The precipitate was filtered off, and the filtrate concentrated by rotary evaporator to a red-brown paste. The paste was dissolved in 4 mL of hot EtOAc, 4 mL of hexanes added, cooled and filtered. The filtrate was purified by flash chromatography on silica gel eluting with an EtOAc/hexanes gradient. Solvent was removed to give a clear glass (0.25 g, 0.51 mmoles, 15%) NMR (300 MHz, CDCl$_3$) δ0.01 (s, 3H), 0.03 (s, 3H), 0.86 (s, 9H), 1.46 (s, 9H), 3.63 (m, 6H), 3.80 (dd, 1H), 4.00 (dd, 1H), 4.20 (m, 4H), 5.33 (d, 1H), 6.73 s, 2H).

e) Preparation of 2-(2-maleimidoethoxy)ethyl L-serinate.

The serine ester prepared above, (0.25 g, 0.51 mmoles) was dissolved in 3 mL of trifluoroacetic acid and stirred for 1 h at room temperature. The solvent was removed by rotary evaporator to give a tan oil. The oil was dissolved in 15 mL of CHCl$_3$, and the solvent removed to give a brown oil. The oil was dried under vacuum overnight. NMR (300 MHz, CD$_3$OD) δ0.04 (s, 3.6H), 0.84 (s, 4.4H), 3.62 (m, 6H), 4.18 (m, 6H), 6.78 (s, 2H).

f) Preparation of 2-(2-maleimidoethoxy)ethyl N-(2-benzoylthioacetyl)serylserylserinate (Compound III).

The deprotected serine ester (0.51 mmoles) was dissolved in 3 mL of THF. To the solution was added the succinimidyl (2-benzoylthioacetyl)serylserinate above (0.29 g, 0.51 mmoles) in 3 mL of DMF. The mixture was stirred at room temperature for 6 h. The THF was removed by rotary evaporator (bath temperature <30°), and water (2 mL) added to give a slightly cloudy suspension. The mixture was purified by repeated flash chromatography on reverse phase silica (C$_{18}$), eluting with a methanol/water gradient. The solvent was removed to give 20 mg of product (0.03 mmoles, 6%). TLC R$_f$0.63 (reverse phase (C$_{18}$) plates, 50% MeOH). NMR (CD$_3$OD)δ3.78 (m, 6H), 3.92 (m, 8H), 4.24 (m, 2H), 4.49 (m, 2H), 4.56 (t, 1H), 6.83 (s, 1H, should be H), 7.53 (t, 2H), 7.67 (t, 1H), 7.99 (d, 2H).

EXAMPLE 10

Coupling of Compound III to Antifibrin and Removal of the S-Benzoyl Group.

Compound III was coupled to Antifibrin Fab, as described in Example 2. Treatment of the conjugate with H$_2$NOH as above gave 2.6 sulfhydryls/mole.

EXAMPLE 11

Technetium Labeling of Antifibrin Modified with Compound III

The technetium labeling of the deprotected Antifibrin-Compound III conjugate was carried out as in Example 7. The radiolabel was 100% protein bound after 15 minutes by gel filtration HPLC.

EXAMPLE 12

Biodistribution of Radiolabeled Antifibrin - Compound III Conjugate

A mouse biodistribution (Table 3) was obtained as in Example 4.

TABLE 3

Mouse Biodistribution of Tc-99m Labeled Antifibrin-Compound III Conjugate

| | % dose/gram | | | | |
|---|---|---|---|---|---|
| | 30 MIN | 1 HR | 2.5 HR | 5 HR | 24 HR |
| BLOOD | 11.5 | 6.95 | 3.05 | 1.54 | 0.32 |
| HEART | 2.94 | 2.21 | 0.85 | 0.48 | 0.15 |
| LUNG | 4.37 | 3.07 | 1.51 | 0.79 | 0.27 |
| LIVER | 4.95 | 4.46 | 2.84 | 1.86 | 0.81 |
| SPLEEN | 2.19 | 1.78 | 0.95 | 0.53 | 0.27 |
| KIDNEYS | 27.36 | 27.22 | 18.27 | 8.19 | 3.33 |
| STOMACH | 0.71 | 0.66 | 0.60 | 0.20 | 0.21 |
| S.I. | 2.82 | 3.67 | 1.65 | 1.12 | 0.20 |
| L.I. | 0.38 | 0.49 | 5.11 | 2.27 | 0.58 |
| MUSCLE | 0.35 | 0.78 | 0.24 | 0.39 | 0.05 |

EXAMPLE 13

Preparation of 2-(2-maleimidoethoxy)ethyl N-(2-benzoylthiozcetyl)serylserylglycinate (Compound IV).

a) Preparation of 2-(2-maleimidoethoxy)ethanol above (2.70 mmoles) was added 10 mL of methylene chloride, and the solution cooled to 0°. To the solution was added 1.11 g of 2,6-di-tertbutyl-4-methylpyridine (2.70 mmoles, 100 mol%) followed by 0.45 mL of trifluoromethanesulfonic anhydride (2.70 mmoles, 100 mol%). The heterogeneous mixture was stirred at 0° for 1 h. The solution was filtered, and to the filtrate was added a solution of 0.47 g of N-tBOC-glycine (2.70 mmoles, 100 mol%) and 0.47 mL of diisopropylethylamine (2.70 mmoles, 100 mol%) in 10 mL of $CH_2Cl_2$. The mixture was stirred for 2 h at room temperature. Ethyl acetate (100 mL) was added and the solution extracted with water (1×50 mL) then dried over Na2SO4. Filtration and removal of solvent gave an oil which was purified by flash chromatography on 100 mL of silica gel. The column was eluted with 400 mL of EtOAc/hexanes 1:1, giving 0.43 g of pure material (1.26 mmoles, 46%). NMR (300 MHz, $CDCl_3$) $\delta 1.45$ (s, 9H), 3.66 (m, 6H) 3.94 (d, 2H), 4.26 (t, 2H), 5.14 (m, 1H), 6.74 (s, 2H).

b) Preparation of 2-(2-maleimidoethoxy)ethyl glycinate

The above protected glycyl ester (0.43 g, 1.26 mmoles) was stirred in trifluoroacetic acid for 1 h at room temp. The solvent was removed and the resulting tan oil was dried under vacuum overnight. NMR ($CD_3OD$) $\delta 3.64$ (m, 6H), 3.87 (s, 2H), 4.36 (m, 2H), 6.83 (s, 2H).

c) Preparation of 2-(2-maleimidoethoxy)ethyl N-(2-benzoylthioacetyl)serylserylglycinate (Compound IV)

The succinimidyl (2-benzoylthioacetyl)serylserinate prepared above (0.59 g, 1.26 mmoles, 100 mol%) was added to the above deprotected glycine ester along with 5 mL of THF, 3 mL of DMF and 0.22 mL of diisopropylethylamine (1.26 mmoles, 100 mol%). The yellow reaction mixture was stirred at room temperature for 6 h. The THF was removed by rotary evaporator (bath temperature <30°). Water (1 mL) was added and the mixture purified by flash chromatography on 75 mL of reverse phase silica ($C_{18}$). The column was eluted with a methanol/water gradient. Fractions containing the product were combined and solvent removed to give a gel which was dried under vacuum over $P_2O_5$ for 24 hr to give a pale yellow powder (0.15 g, 0.25 mmoles, 20%). TLC R f 0.08 (reverse phase ($C_{18}$) plates, 10% MeOH). NMR (300 MHz, DMSO-$d_6$) $\delta 3.57$ (m, 10H), 3.80 (d, 2H), 3.91 (s, 2H), 4.08 (m, 2H), 4.37 (m, 2H), 4.88 (t, 1H), 5.11 (t, 1H), 7.03 (s, 2H), 7.57 (t, 2H), 7.69 (t, 1H), 7.93 (d, 2H), 8.08 (d, 1H), 8.19 (t, 1H), 8.36 (d, 1H).

EXAMPLE 14

Coupling of Compound IV to Antifibrin and Removal of the S-Benzoyl Group

Compound IV was coupled to Antifibrin Fab' as detailed in Example 2. Treatment of the conjugate with H2NOH as above gave 2.5 sulfhydryls/mole.

EXAMPLE 15

Technetium Labeling of Antifibrin Modified with Compound IV

The technetium labeling of the deprotected Antifibrin-Compound IV conjugate was accomplished as described in Example 7. The radiolabel was 100% protein bound after 15 minutes by gel filtration HPLC.

EXAMPLE 16

Preparation of 2-(2-maleimidoethylamino)-2-oxoethyl (2-(3-carboxybenzoylthio)acetyl)glycylglycylglycinate (Compound V)

a) Preparation of 2-(tert-butyloxycarbonylamino)ethylamine.

To a solution of 7.5 g of aminoacetontrile hydrochloride (81.05 mmoles, 150 mol%) and 10.0 g of $NaHCO_3$ (119 mmoles, 220 mol%) in 150 mL of water was added 11.9 g of di-tert-butyl dicarbonate (54.4 mmoles). The heterogeneous mixture was stirred vigorously for 16 h at room temperature. The pH was adjusted to 5.0 with 2 N HCl. The solution was extracted with ethyl acetate (2×75 mL) and the extracts dried over $Na_2SO_4$. Filtration and removal of solvent by rotary evaporator gave a brown oil. Kugelrohr distillation gave a fraction bp 95°, 0.10 mmHg as a low melting white solid (8.20 g, 52.5 mmoles, 96%). TLC $R_f$ 0.74(EtOAc), $R_f$ 0.61(EtOAc/hexanes 1:1). In a Parr pressure bottle was placed 2.0 g of the above protected nitrile and 75 mL of glacial acetic acid. After the protected nitrile had dissolved, 0.20 g of 5% Pd/C was added and the mixture hydrogenated at 45 psig $H_2$ for 2 h. The mixture was filtered through acid-washed celite, and the acetic acid removed by rotary evaporator (30°, vacuum pump) to give a tan oil. NMR ($CDCl_3$) 1.32 (s, 9H), 2.58 (m, 2H), 3.15 (m, 2H).

b) Preparation of N-(2-tert-butyloxycarbonylamino)ethylmaleimide.

The crude N-t-BOC-ethylenediamine prepared above (1.2 g) was dissolved in 25 mL of ice cold saturated $NaHCO_3$ and placed in an ice bath. To this solution was added 0.78 g of N-methoxycarbonylmalemide (5.0 mmoles, 100 mol%). The heterogeneous mixture was stirred vigorously for 20 min at 0°, followed by 1 h at room temperature. Water (50 mL) was added and the mixture extracted with chloroform (2×50 mL). The extracts were dried over $Na_2SO_4$, filtered and the solvent removed to give a white solid. Recrystallization from EtOAc/hexanes gave 0.70 g of product (2.91 mmoles, 58%). NMR showed 35% contamination with an N-carbomethoxy intermediate. NMR (300 MHz, DMSO-$d_6$) δ1.33 (s, 9H), 3.05 (m, 2H), 3.36 (s, 1H, impurity), 3.42 (m, 2H), 7.01 (s +m, 2H).

c) Preparation of N-(2-bromoacetamidoethyl)maleimide.

The crude maleimide described above (0.70 g, 2.91 mmoles) was dissolved in 5 mL of trifluoroacetic acid and stirred at room temperature for 1 h. The acid was removed by rotary evaporator to give a tan oil. Chloroform (20 mL) was added and the solvent removed to give a brown oil. This oil was dried under vacuum for 2 h. The oil was dissolved in 10 mL of $CHCl_3$ and cooled to 0°. Water (20 mL), $NaHCO_3$ (0.98 g, 11.65 mmoles, 400 mol%) and bromoacetyl bromide (0.30 mL, 3.50 mmoles, 120 mol%) were added and the mixture stirred vigorously for 1 h. Additional water (30 mL) and $CHCl_3$ (30 mL) were added, and the mixture extracted. The aqueous layer was washed with an additional 30 mL of $CHCl_3$. The combined extracts were dried over $Na_2SO_4$, filtered and the solvent removed to give a light brown solid (0.11 g, 0.42 mmoles, 14%). NMR (300 MHz, $CDCl_3$)δ 3.52 (m, 2H), 3.75 (m, 2H), 3.85 (s, 2H), 6.76 (s+br m, 3H).

d) Preparation of 2-(2-maleimidoethylamino)-2-oxoethyl 2-(3-tert-butyloxycarbonylbenzoylthio)acetylglycylglycylglycinate.

The above N-(2-bromoacetamidoethyl)maleimide (0.36 g, 1.38 mmoles) was dissolved in 10 mL of dry DMF. To this solution was added 0.66 g of (2-(3-tert-butyloxycarbonylbenzoylthio)acetyl)glycylglycylglycine (1.38 mmoles, 100 mol%), 0.24 mL of diisopropylethylamine (1.38 mmoles, 100 mol%) and 0.18 g of lithium iodide (1.38 mmoles, 100 mol%). The flask was stoppered, covered in foil and the contents stirred at room temperature for 18 h. Water (5 mL) was added to give a cloudy solution. The mixture was then purified by flash chromatography on 75 mL of reverse phase silica ($C_{18}$). The column was eluted with a methanol/water gradient. The solvent was removed from fractions containing the product, and the solid dried under vacuum to give a white powder (0.17 g, 0.26 mmoles, 19%). NMR (300 MHz, $CDCl_3/CD_3OD$) δ1.63 (s, 13H, should be 9H), 3.95 (m, 6H) 4.04 (s, 2H), 4.51 (s, 2H), 4.55 (m, 1H), 6.78 (s, 2H), 7.62 (t, 1H), 8.19 (d, 1H), 8.21 (d, 1H), 8.54 (s, 1H).

e) Preparation of 2-(2-maleimidoethylamino)-2-oxoethyl (2-(3-carboxybenzoylthio)acetyl)glycylglycylglycinate (Compound V).

The above 2-(2-maleimidoethylamino)-2-oxoethyl ester (16 mg) was stirred in trifluoroacetic acid for 1 h and the solvent removed. The resultant pale yellow glass was dried under vacuum overnight. NMR (DMSO-$d_6$) δ3.25 (dt, 2H), 3.47 (t, 2H), 3.78 (m, 4H), 3.93 (two s, 4H), 4.40 (m, 2H), 7.00 (s, 2H), 7.72 (t, 2H), 8.20 (m, 5H), 8.44 (s+t, 2H)

EXAMPLE 17

Coupling of Compound V to Antifibrin and Removal of the S-Benzoyl Group

Compound V was coupled to Antifibrin Fab' as described in Example 2. Treatment of the conjugate with H2NOH as above gave 0.7 sulfhydryls/mole.

EXAMPLE 18

Technetium Labeling of Antifibrin Modified with Compound V

The technetium labeling of the deprotected Antifibrin-Compound V conjugate was carried out as in Example 7. The radioactivity was 100% protein bound after 15 minutes by gel filtration HPLC.

EXAMPLE 19

Biodistribution of Radiolabeled Antifibrin-Compound V Conjugate

A mouse biodistribution (Table 4) was obtained as in Example 4.

TABLE 4

| Mouse Biodistribution of Tc-99m Labeled Antifibrin-Compound V Conjugate | | | | | |
|---|---|---|---|---|---|
| | % dose/gram | | | | |
| | 30 MIN | 1 HR | 2.5 HR | 5 HR | 24 HR |
| BLOOD | 13.18 | 10.19 | 3.56 | 1.49 | 0.23 |
| HEART | 3.02 | 2.79 | 0.95 | 0.43 | 0.09 |
| LUNG | 4.27 | 3.60 | 1.61 | 0.82 | 0.16 |
| LIVER | 3.09 | 2.79 | 1.65 | 1.40 | 0.36 |
| SPLEEN | 1.98 | 1.35 | 0.67 | 0.41 | 0.12 |
| KIDNEYS | 28.97 | 22.39 | 16.10 | 12.73 | 4.04 |
| STOMACH | 2.05 | 1.14 | 0.55 | 0.60 | 0.20 |
| S.I. | 2.08 | 3.44 | 2.77 | 1.49 | 0.20 |
| L.I. | 0.40 | 0.45 | 3.95 | 5.98 | 0.62 |
| MUSCLE | 0.40 | 0.63 | 0.35 | 0.18 | 0.03 |

EXAMPLE 20

Coupling of compound V to Antimyosin and Removal of the S-Benzoyl Group

Compound V was coupled to Antimyosin Fab' as described in Example 2. Upon exposure to H2NOH as above, 1.7 sulfhydryls/mole were generated.

EXAMPLE 21

Technetium Labeling of Antimyosin Modified with Compound V

The deprotected Antimyosin-Compound V conjugate was Tc-99cm labeled as in Example 7. After 15 minutes, the radioactivity was 100% protein bound by gel filtration HPLC.

EXAMPLE 22

Dog Model Infarct and Biodistribution Study of Radiolabeled Antimyosin - Compound V Conjugate The [Tc-99m]Antimyosin - Compound V conjugate and [In-111]Antimyosin Fab-DTPA were coinjected into a dog in which an experimental myocardial infarct had been induced. The biodistribution data comparing the two radiolabeled products are presented in Table 5.

TABLE 5

Dog Model Infarct Study Comparing Tc-99m Labeled Antimyosin Fab'-Compound V Conjugate to In-111 Labeled Antimyosin Fab-DTPA Conjugate

| Organ | Tc-99m | In-111 |
|---|---|---|
| | % Activity/Gram | |
| Spleen | 0.003 | 0.004 |
| Liver | 0.008 | 0.019 |
| Kidney (Cortex) | 0.045 | 0.091 |
| (Medulla) | 0.028 | 0.116 |
| | % Injected dose/organ | |
| Heart (Normal) | 0.005 | 0.007 |
| (Infarct) | 0.050 | 0.060 |

EXAMPLE 23

Preparation of 14-(N-maleimido)-5-oxo-3,6,9,12-tetraoxatetradecyl (2-(3-carboxybenzoylthio)acetyl)glycylglycylglycinate (Compound VI)

a) Preparation of mono-2,2,2-trichloroethyl diglycolate.

A solution of 2,2,2-trichloroethanol (8.5 g, 57 mmoles) and diglycolic anhydride (6.6 g, 57 mmoles) in pyridine (35 ml) was heated at 90° C. for 2 hours and stirred at room temperature overnight. Pyridine was removed under reduced pressure. The residue was taken up in $CH_2Cl_2$ and washed with 1 N HCl (2×), brine, and dried over $Na_2SO_4$. Removal of the solvent gave the half ester as an oil (12 g, 80%). NMR (CDCl3) δ4.40 (s, 2H), 4.50 (s, 2H), 4.88 (s, 2H).

b) Preparation of 2,2,2,-trichloroethyl 3-oxa-5-hydroxypentanoate

A solution of the above half ester (6.0 g, 22 mmoles) in THF (70 mL) was cooled in an ice bath and treated dropwise with 1 M borane-THF (30 mL, 30 mmoles). After stirring 3 hours, methanol was added and the solvent removed by rotary evaporator. The residue was taken up in $CH_2Cl_2$ and washed with $NaHCO_3$ (sat.), and dried over $Na_2SO_4$. Removal of the solvent gave an oil which was distilled at the Kugelrohr. The alcohol (2.6 g, 46%) was collected between 90° and 100° C. at 0.6 mmHg. NMR (CDCl3) 2.70 (s, 1H, OH) 3.78 (m, 4H), 4.37 (s, 2H), 4.83 (s, 2H).

c) Preparation of 5-(2,2,2-trichloroethyloxycarbonyl)-3-oxapentyl (2-(3-tert-butyloxycarbonylbenzoylthio)acetyl)glycylglycylglycinate.

A solution of the above hydroxy ester (0.65 g, 2.6 mmoles) in $CH_2Cl_2$ (6 mL) was cooled in an ice bath and treated with 2,6-di-t-butyl-4-methylpyridine (0.57 g, 2.8 mmoles) followed by the addition of a solution of trifluoromethanesulfonic anhydride (0.47 ml, 2.8 mmoles) in $CH_2Cl_2$ (2 mL). After stirring for 45 minutes the mixture was filtered and added to a solution of 2-(3-tertbutyloxycarbonylbenzoylthio)acetylglycylglycylglycinate (1.0 g, 2.1 mmol) and Hunig's base (diisopropylethylamine) (380μ/L, 2.2 mmoles) in $CH_2Cl_2$ (10 mL). After stirring for 3 hours the mixture was concentrated and chromatographed ($SiO_2$, $CH_2Cl_2$-$CH_3OH$ gradient). Fractions containing product were concentrated and washed with 1N HCl, and dried over $Na_2SO_4$. Removal of solvent gave the diester as a white solid (0.64 g, 43%). NMR (CDCl3) δ1.66 (s, 9H), 3.89 (m, 4H), 4.08 (m, 6H), 4.37 (m, 4H), 4.88 (s, 2H), 7.02 (t, 1H), 7.18 (t, 1H), 7.34 (t, 1H), 7.60 (t, 1H), 8.17 (d, 1H), 8.29 (d, 1H), 8.62 (s, 1H).

d) Preparation of 5-carboxy-3-oxapentyl (2-(3-tert-butyloxycarbonylbenzoylthio)acetyl)glycylglycylglycinate.

The above 5-(2,2,2-trichloroethyloxycarbonyl)-3-oxapentyl ester (0.6 g, 0.85 mmoles) was dissolved in THF (20 mL) containing 1 M aqueous $KH_2PO_4$ (4 mL) and acetic acid (1 mL). Zinc (2 g, 30 mmoles) was added and the mixture was stirred for 1 hour, filtered, and diluted with THF. Zinc salts were filtered off and the filtrate was taken to dryness at the rotary evaporator. The residue was chromatographed ((C-18), water-methanol gradient) to give the acid as a white powder (0.16 g, 33%). NMR (CD3OD) δ1.62 (s, 9H), 3.75 (s, 2H), 3.94 (m, 8H), 4.06 (s, 2H), 4.28 (s, 2H), 7.62 (t, 1H), 8.20 (m, 2H), 8.52 (s, 1H).

e) Preparation of 8-azido-3,6-dioxaoctanol.

A mixture of 8-chloro-3,6-dioxaoctanol (16.8 g, 100 mmol) and $NaN_3$ (13 g, 200 mmol) in DMF (300 mL) was stirred at 90° C. for 14 hours. Most of the solvent was removed under vacuum and the residue was taken up in water and extracted with ethyl acetate. The combined organic extracts were washed with brine and dried over $Na_2SO_4$. Removal of the solvent gave the azide as an oil (12.1 g, 69%). NMR (CDCl3) δ3.66 (m, 12H).

f) Preparation of 8-amino-3,6-dioxaoctanol.

A mixture of 8-azido-3,6-dioxaoctanol (3.0 g, 17 mmoles) and 10% Pd/C (0.3 g) in methanol (30 mL) was hydrogenated at 45 psig for 1 hour. The catalyst was removed by filtration through celite and the solvent was removed to provide the amine (2.6 g, 100%). NMR (CDCl3) δ2.62 (s, 2H, $NH_2$), 2.79 (m, 2H), 3.53 (m, 10H).

g) Preparation of 8-maleimido-3,6-dioxaoctanol.

The above amine (2.3 g, 15 mmoles) in sat. $NaHCO_3$ (80 mL) was cooled in an ice bath and treated with N-methoxycarbonyl maleimide (2.4 g, 15 mmoles). After stirring 30 minutes the ice bath was removed and stirring was continued for an additional 30 minutes. The solution was extracted with $CH_2Cl_2$ and the combined extracts were dried over $Na_2SO_4$. Removal of the solvent under reduced pressure gave the crude maleimide which was chromatographed ($SiO_2$ ethyl acetate-hexanes gradient) to yield pure product (2.1 g, 60%) as an oil. NMR (CDCl3) δ2.81 (s, 1H, OH), 3.70 (m, 12H), 6.74 (s, 2H).

h) Preparation of 14-(N-maleimido-5-oxo-3,6,9,12-tetraoxatetradecyl)(2-(3-tert-butyloxycarbonylbenzoylthio)acetyl)glycylglycylglycinate.

A solution of 8-maleimido-3,6-dioxaoctanol (0.075 g, 0.33 mmoles) and 2,6-di-t-butyl-4-methylpyridine (0.074 g, 0.36 mmoles) were dissolved in $CH_2Cl_2$ (1 mL) and cooled in an ice bath. To this solution was added trifluoromethanesulfonic anhydride (60μL, 0.36 mmoles) in $CH_2Cl_2$ (0.5 mL). After stirring for 45 minutes, the mixture was filtered, and the filtrate was added to a solution of the above 5-carboxy-3-oxapentyl ester (0.15 g, 0.27 mmoles) and Hunig's base (50 μL, 0.27 mmoles) in $CH_2Cl_2$ (1.5 mL). After stirring for 3 hours the mixture was concentrated and chromatographed ($SiO_2$, $CH_2Cl_2$-$CH_3OH$ gradient). Fractions containing product were pooled and washed with 1 N HCl and dried over $Na_2SO_4$. Removal of the solvent gave the ester (0.076 g, 37%). NMR (CDCl3—CD3OD) δ1.62 (s, 9H), 3.68 (m, 10H), 3.82 (s, 2H), 3.99 (m, 8H), 4.17 (s, 2H), 4.30 (m, 4H), 6.74 (s, 2H), 7.52 (t, 1H), 8.08 (d, 1H), 8.21 (d, 1H), 8.53 (s, 1H).

i) Preparation of 14-(N-maleimido)-5-oxo-3,6,9,12-tetraoxatetradecyl (2-(3-carboxybenzoylthio)acetyl)-glycylclycylglycinate (Compound VI).

The 2-(3-tert-butyloxybenzoylthio)acetyl derivative above (0.07 g, 0.09 mmoles) was stirred in TFA (0.5 mL) for one hour. After removal of excess TFA under vacuum, the product was obtained as an oil. NMR (DMSO-d$_6$) δ3.52 (m, 10H), 3.79 (m, 10H), 3.92 (s, 2H), 4.18 (m, 4H), 7.02 (s,2H), 7.73 (t, 1H), 8.18 (d,1), 8.25 (m, 3), 8.42 (s, 1H), 8.55 (t, 1H).

EXAMPLE 24

Coupling of Compound VI to Antifibrin and Removal of the S-Benzoyl Group

Compound VI was coupled to Antifibrin as outlined in Example 2. Treatment with H$_2$NOH as above yielded 1.3 sulfhydryl/mole.

EXAMPLE 25

Technetium Labeling of Antifibrin Modified with Compound VI

The technetium labeling of the deprotected Antifibrin Compound VI conjugate was carried out as in Example 3. After 15 minutes, 100% of the radioactivity was protein bound by paper chromatography.

Example 26

Biodistribution of Radiolabeled Antifibrin - Compound VI Conjugate

A mouse biodistribution (Table 6) was obtained as in Example 4.

TABLE 6

Mouse Biodistribution of Tc-99m Labeled Antifibrin-Compound VI Conjugate

| Time (hrs.) | % dose/gram | | | |
|---|---|---|---|---|
| | 0.5 | 1.0 | 3.0 | 5.5 |
| Organ | | | | |
| BLOOD | 13.58 | 9.0 | 3.89 | 1.78 |
| HEART | 2.92 | 2.18 | 0.82 | 0.43 |
| LUNGS | 3.98 | 3.48 | 1.67 | 0.84 |
| LIVER | 5.2 | 4.8 | 4.11 | 2.91 |
| SPLEEN | 2.53 | 2.05 | 1.55 | 0.79 |
| KIDNEYS | 26.15 | 22.14 | 15.16 | 9.2 |
| STOMACH | 1.1 | 1.05 | 0.8 | 0.44 |
| S.I. | 4.46 | 5.36 | 3.76 | 1.41 |
| L.I. | 0.44 | 0.68 | 6.04 | 15.93 |
| MUSCLE | 0.39 | 0.38 | 0.35 | 0.17 |

EXAMPLE 27

Coupling of Compound VI to Antimyosin and Removal of the S-Benzoyl Group

Compound VI was coupled to Antimyosin Fab' as described in Example 2. After treatment with H$_2$NOH as above, 3 sulfhydryls/mole were present.

EXAMPLE 28

Technetium Labeling of Antimyosin Modified with Compound VI

The deprotected Antimyosin-Compound VI conjugate was Tc-99m labeled as in Example 3. After 1.75 hours, 96% of the radioactivity was protein bound by gel filtration HPLC. The product was 85% immunoreactive as determined by affinity chromatography.

EXAMPLE 29

Dog Model Infarct and Biodistribution Study of Radiolabeled Antimyosin-Compound VI Conjugate The [Tc-99m]Antimyosin-Compound VI conjugate and [In-111]Antimyosin Fab-DTPA were coinjected into a dog in which an experimental myocardial infarction had been induced. Biodistribution data comparing the two radiolabeled products are presented in Table 7.

TABLE 7

Dog Model Infarct Study
Comparing Tc-99m Labeled Antimyosin Fat'-Compound VI Conjugate to In-111 Labeled Antimyosin Fab-DTPA Conjugate

| Organ | % activity/gram | |
|---|---|---|
| | Tc-99m | In-111 |
| Kidney cortex | 0.0216 | 0.1204 |
| Kidney medulla | 0.0144 | 0.0947 |
| Liver | 0.0057 | 0.0173 |
| Lung | 0.0047 | 0.0115 |
| Bile | 0.1392 | 0.0118 |
| Urine | 0.0527 | 0.0269 |
| Infarct to Normal | 14 | 11 |
| Blood half-life (minutes) | 70 | 120 |

What is claimed is:

1. A bifunctional coupling agent which has the formula selected from the group consisting

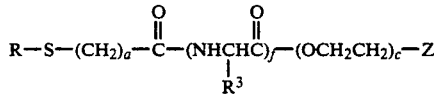

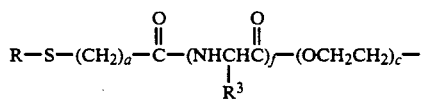

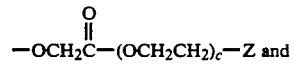

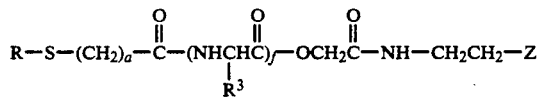

wherein a is an integer from 1 to 3 inclusive; c is an integer from 1 to 7 inclusive; f is an integer from 3 to 6 inclusive; R is R$^1$CO— or R$^1$S—, wherein R$^1$ is selected from the group consisting of lower alkyl; lower alkyl substituted with one or more groups selected from the group consisting of alkoxy groups, alkyl groups, aryl groups, hydroxy groups and carboxy groups; aryl; and aryl substituted with one or more groups selected from the group consisting of alkoxy groups, alkyl groups, aryl groups, hydroxy groups and carboxy groups; R$^3$ is selected from hydrogen, optionally substituted lower alkyl, and optionally substituted aryl; and Z is maleimido.

2. The bifunctional coupling agent of claim 1 which has the formula:

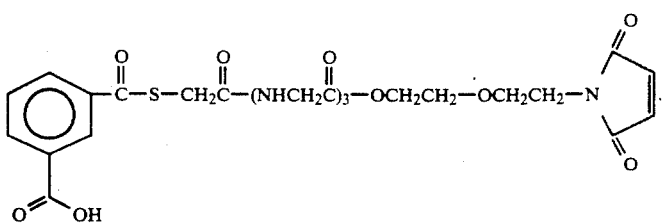
3. The bifunctional coupling agent of claim 1 which has the formula:
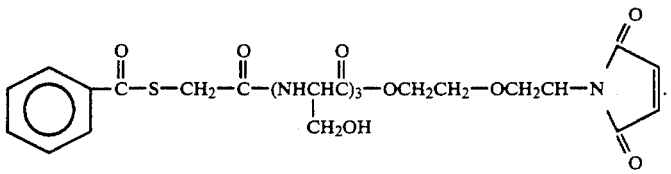
4. The bifunctional coupling agent of claim 1 which has the formula:
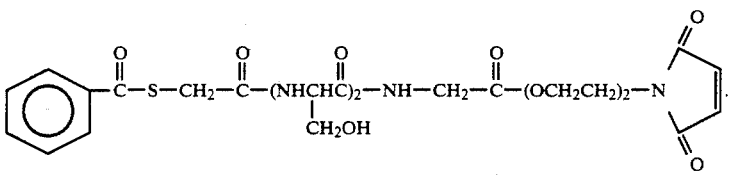
5. The bifunctional coupling agent of claim 1 which has the formula:
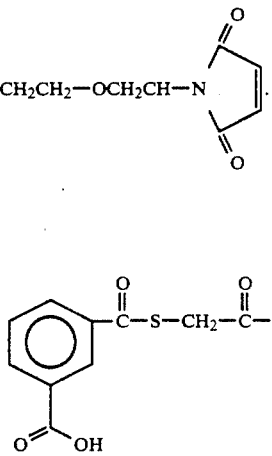
6. The bifunctional coupling agent of claim 1 which has the formula:
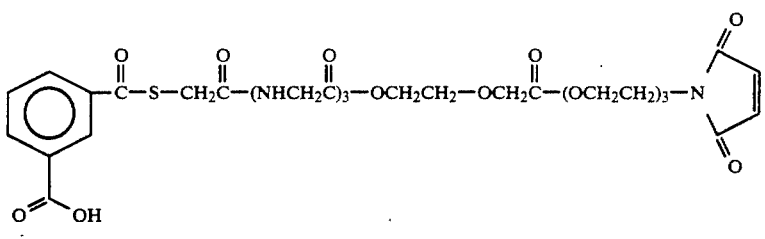
* * * * *